United States Patent [19]

Bryant

[11] 4,448,767

[45] May 15, 1984

[54] PREPARATION OF MONOSPECIFIC MALE-SPECIFIC ANTIBODY AND THE USE THEREOF FOR INCREASING THE PERCENTAGE OF MAMMALIAN OFFSPRING OF EITHER SEX

[75] Inventor: Bernard J. Bryant, Davis, Calif.

[73] Assignee: Sumar Corporation, Foster City, Calif.

[21] Appl. No.: 117,341

[22] Filed: Feb. 15, 1980

Related U.S. Application Data

[63] Continuation-in-part of Ser. No. 841,207, Oct. 11, 1977, Pat. No. 4,191,749.

[51] Int. Cl.³ .................. A61K 39/00; A61K 35/48
[52] U.S. Cl. ............................. 424/85; 424/105; 435/2
[58] Field of Search ............... 424/85, 105; 435/1, 435/2

[56] References Cited

U.S. PATENT DOCUMENTS 3,687,806  8/1972  Bovenkamp ............ 424/85
3,692,897  9/1972  Bhattacharya .......... 424/85

OTHER PUBLICATIONS

Schnieders et al.–Chem. Abst. vol. 82, (1975) p. 15,070q.

Primary Examiner—Sam Rosen
Attorney, Agent, or Firm—Townsend & Townsend

[57] ABSTRACT

A method of manufacturing and a raw material and its useage are disclosed for increasing the percentage of mammalian offspring of either sex. The process of use utilizes a male-specific antibody coupled to a solid-phase immunoabsorbent material to effect a separation of sex-determining spermatozoa derived from a semen suspension. The male-specific antibody selectively binds male-determining spermatozoa, while the female-determining spermatozoa remain not bound and are recoverable. A male specific antibody that is monospecific is prepared from male cells subjected to a multi-step process which includes using said cells for the hyperimmunization of a female species and the preparation of an antiserum which is purified as to specificity by a multiplicity of absorptions against female cells. The antiserum is fractionated to yield male specific monospecific immunoglobulin which may be used to effect a separation of sex determining spermatozoa.

7 Claims, 2 Drawing Figures

PREPARATION OF MONOSPECIFIC MALE-SPECIFIC ANTIBODY AND THE USE THEREOF FOR INCREASING THE PERCENTAGE OF MAMMALIAN OFFSPRING OF EITHER SEX

The present application is a continuation-in-part of copending U.S. patent application Ser. No. 841,207, Oct. 11, 1977 now U.S. Pat. No. 4,191,749, of Bernard J. Bryant for Method and Material for Increasing the Percentage of Mammalian Offspring of Either Sex.

BACKGROUND OF THE INVENTION

1. Field of the Invention

My invention relates to a method of manufacture of a raw material and the process which utilizes it for increasing the percentage of mammalian offspring of either sex, and more particularly to immunological method of increasing the percentage of mammalian offspring of either sex.

2. Description of the Prior Art

Mechanical methods increasing the percentage of mammalian offspring of either sex by providing seminal fluids containing a surplus of either male-determining spermatozoa or female-determining spermatozoa with the aid of the difference in density between male-determining spermatozoa and female-determining spermatozoa are taught in the prior art, e.g., in abandoned U.S. patent application Ser. No. 443,473, in U.S. patent application Ser. No. 814,906, and in a paper by E. Schilling, "Separation of Bull Sperm by Sedimentation and Centrifugation and the Sex of the Born Cows," *Zeitschrift fur Saugertierkunde,* Volume 31, No. 4, pages 314–323 (1960). Such methods are known, however, to be characterized by reduced sperm survivability, and by reduced viability of the surviving sperm.

The speculation that immunological means can be used to increase the percentage of mammalian offspring of either sex is discussed in a paper entitled "Sex Ratio In Progeny of Mice Inseminated with Sperm Treated with H-Y Antiserum" by Bennett and Boyse, *Nature,* Volume 246, Nov. 30, 1973, pages 308 and 309.

An immunological method of increasing the percentage of mammalian offspring of either sex is disclosed in U.S. Pat. No. 3,687,806, issued to Gustaaf J. van den Boevenkamp on Aug. 29, 1972. The method of this patent required as a starting material a sperm fraction containing a surplus of either male-determining spermatozoa or female-determining spermatozoa isolated in accordance with the aforementioned abandoned application Ser. No. 443,473, the other above-mentioned application Ser. No. 814,906, or the aforementioned Schilling article, or closely related mechanical methods. Thus, the method of the aforementioned U.S. Pat. No. 3,687,806 necessarily suffers to a greater or lesser degree from the disadvantages of said mechanical methods, i.e., reduced sperm survival and reduced viability of the surviving sperm.

Electrophoresis and other processes are known to the art for sperm separation as well, and those all have their respective shortcomings.

SUMMARY OF THE INVENTION

Accordingly, it is an object of the present invention to provide an immunological method of increasing the percentage of mammalian offspring of either sex without subjecting the required seminal fluid to mechanical separation techniques depending upon the very small density differential between male-determining spermatozoa and female-determining spermatozoa.

In general, it is an object of the present invention to provide a successful method for preselecting the sex of mammalian offspring, which utilizes a monospecific male-specific antibody prepared according to a process disclosed herein.

Yet another object of the present invention is to provide a product for use in the artificial insemination of mammalian females made from monospecific male-specific or female-specific antibodies containing a very substantial preponderance of either male-determining spermatozoa or female-determining spermatozoa.

In another object of the present invention, a Y-antigen specific antibody (hereinafter sometimes called "male-specific antibody" or "anti-Y antibody") is prepared and coupled to an immunoabsorbent material.

In accordance with another object of the present invention, a male-specific antibody-coupled solid-phase immunoabsorbent material is used to selectively and solely bind male-determining spermatozoa (hereinafter sometimes called "Y-sperm") contained in a sperm suspension, so that female-determining spermatozoa (sometimes hereinafter called "X-sperm") can be directly recovered.

In accordance with another feature of the present invention, a means is provided for releasing immunoabsorbent-bound Y-sperm so that Y-sperm can be recovered.

One of the primary objects however, of the present invention, is to provide an immunoabsorbent-coupled male-specific antibody which binds selectively and solely to the Y-antigen, and to no other antigen, expressed on mammalian sperm surface membranes In accordance with another aspect of the present invention, method and apparatus are provided by which a given batch of male-specific antibody-coupled immunoabsorbent material can be tested for efficacy prior to use in mammalian sperm fractionation. Yet another object is the isolation of a product designated as monospecific male-specific antibody.

Other objects of the invention will in part be obvious and will in part appear hereinafter.

My invention, accordingly, comprises the several steps and the relation of one or more of such steps with respect to each of the others, combinations and arrangements of parts which are adapted to effect such steps, and the material which possesses the characteristics and properties, all as exemplified in the detailed disclosure hereinafter set forth, and the scope of the invention which will be indicated in the appended claims.

For a fuller understanding of the nature and objects of the invention, reference should be had to the following detailed description, taken in connection with the accompanying drawings.

DETAILED DESCRIPTION OF THE PREFERRED EMBODIMENTS

Figure 2:
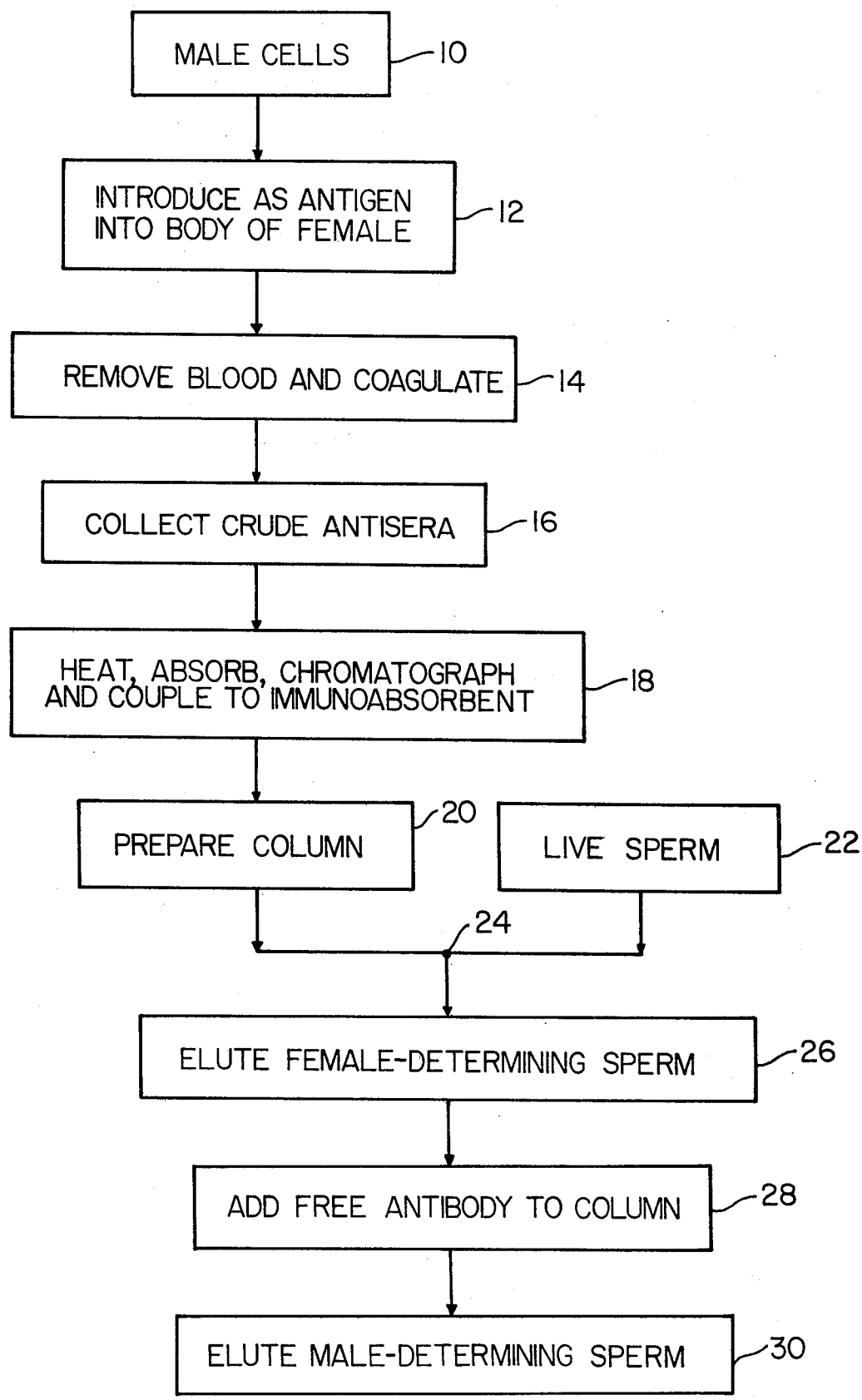
FIG. 2 is a flow sheet illustrating in more general terms, the process of making the raw material for use in the method of using same for the selection of mammalian offspring.

As shown more particularly in FIG. 2, the method of my total invention comprises preparing a male-specific antibody (sometimes called a "Y antigen-specific antibody" or "anti-Y antibody"): coupling said male-specific antibody to a solid-phase immunoabsorbent material; adding unseparated spermatozoa to said male-specific antibody coupled solid-phase immunoabsorbent material and eluting female-determining spermatozoa directly; treating said solid-phase immunoabsorbent material containing bound male-determining sperm to inhibit the binding of the male-determining spermatozoa; and eluting the male-determining spermatozoa from said solid-phase immunoabsorbent material. The coupling of the male specific antibody after preparation, to an immunoabsorbent material and the use of same from artificial insemination is disclosed and claimed in my patent application Ser. No. 841,207, filed Dec. 11, 1977, and soon to be U.S. Pat. No. 4,191,749. The disclosure of the application is expressly incorporated herein by references.

Experience with the method of my invention leads to the expectation that by its use seminal fluids [i.e., fluids suitable for use in artificial insemination, containing a substantial preponderance of male-determining spermatozoa or female-determining spermatozoa (Y-sperm or X-sperm)] may be provided which contain ten percent or fewer of undesired spermatozoa, and that those seminal fluids are fertile in artificial insemination and are strongly preselective for the desired sex of the offspring. Experience also shows that a male-specific antibody prepared in one mammalian species by the method of my invention can be used to separate sex-determining spermatozoa of other mammalian species, i.e., the male-specific antibody is to some extent immunologically cross-reactive between species.

Figure 1:
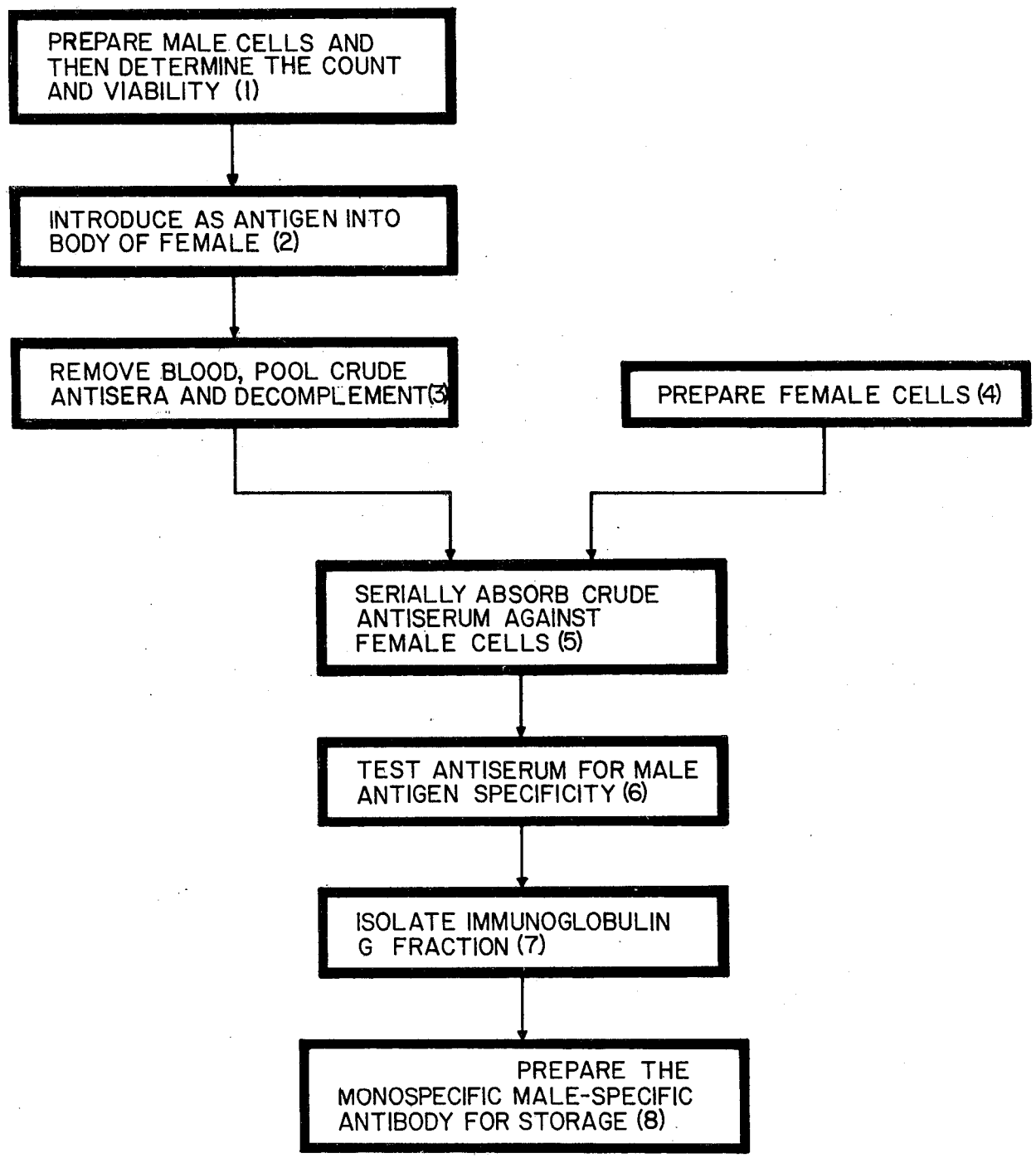
FIG. 1 is a flow sheet illustrating the method of making the monospecific male-specific antibody of this invention.

Referring now to FIG. 2, there is seen a generalized example illustrating the practice of the total method of my invention, while FIG. 1 provides more details of a portion of the total FIG. 2 process. It is to be understood, however, that my invention is not limited to the particular methods, immunoabsorbent, and seminal fluids described in detail hereinbelow, since many variations in the below-described specific methods, and the components thereof will occur to those having ordinary skill in the art of immunology, upon being informed by my present disclosure, without the exercise of invention.

The technique of isolating male-specific antibody selected for use in carrying out the generalized process of the total method of by invention is the technique of animal immunization with Y antigen. As is known in the art, male-specific antibody can be isolated from the blood sera in which it occurs by several other techniques well-known in the art of immunology. However, such techniques are not monospecific. That is, these processes of the prior art prepare male-specific antibodies which contain or include many or all undesired antibodies, i.e., other antibodies which interact and combine with other antigens on the surfaces of male and female cells. Thus the prior art did not isolate for male monospecificity.

The following animal immunization technique, based upon the fact that Y antigen capable of eliciting male-specific antibody in the blood of female recipients is found on epidermal and other cells and sperm heads of small rodents & other male animals, may be used to provide the male-specific antibody required for carrying out the immunoabsorbent coupling process claimed in my parent application.

Female rabbits are hyper-immunized by intraperitoneally injecting 500 million trypsin-dissociated epidermal cells from male rabbits in a series of twice-weekly injections lasting 6 weeks. Six days after the last injection the female rabbits are exsanguinated. The blood samples thus obtained are allowed to clot and crude antisera are isolated, complement-inactivated by heating at 56° C. for 30 minutes, and then pooled. All other antibodies are then removed from the crude antiersum pool by a series of fifteen repeated absorptions against packed, washed female rabbit spleen cells combined from several individuals. The absorbed antiserum pool is finally fractionated by agarose gel filtration according to the method of Hannon (Journal of Immunological Methods, 1975, 8:29). The fraction representing gamma globulin G is isolated and stored at $-20°$ Celsius until used in further carrying out of the method of my invention, as shown in FIG. 2, wherein the monospecific male-specific antiserum or antibody as it is often called, is coupled to a solid-phase immunoabsorbent material, as noted by reference numeral 18 of said FIG. 2. Having described the preparation of the antiserum in brief, I shall now describe same in detail.

Specifically, it is seen that the process for the preparation of the monospecific male-specific antibody as a product first requires the preparation of male cells and the determination of the count, i.e. the amount of and the viability of same. Once these are accounted for, they are introduced as an antigen into the body of a female of the species, such as a female rabbit. While rabbits were employed for the laboratory efforts, any rodent may be so employed, primarily due to low cost. However, it is to be understood that any mammal female can be used. Indeed, it need not be the same mammalian genus that will be artifically inseminated according to the process described in my parent application using the coupled immunoabsorbent, into which the antigen is introduced.

The male cells are obtained from rabbits such as adult male New Zealands by removing skin such as readily removeable thoracic skin from freshly killed specimens. The skin is placed in a balanced salt solution of approximately neutral pH, such as Hank's balanced salt solution, a staple article of commerce known to the trade, and which has a pH of about 7.4. This representative solution was used for several steps of the process and therefore will be referred to as HBSS for the convenience of the reader.

A cell dissociater is added to the HBSS and skin segment are permitted to incubate until the cells dissociate into individual cells, usually about one hour, under mild heat. Any compatible dissociateer may be employed, though a 0.1% addition of trypsin is commonly employed. Another dissociater that can be used is deoxyribonuclease, but due to its high cost, about 20 to 30 times more than trypsin, this is generally employed for residual cell breakup after a pretreatment with the trypsin and a screening or sieving through fine multiple layered nylon mesh and a period of centrifugation. This secondary treatment with deoxyribonuclease dissociates any remaining cellular aggregates and small clumps. Obviously such a secondary technique is an optional one, to achieve better yields.

In the alternative, two different cell dissociaters could be employed for the initial breakdown step if desired. Thus pronase is believed to be a suitable reagent for cell dissociation as well.

After incubation and seiving, the epidermal cells are centrifuged or otherwise separated. While separation at 1 g by sedimentation may occur, separation by centrifugation by from about 10 g to about 5000 g's and conveniently at about 100 g is preferred Subsequent to washing and re-suspension in HBSS, an aliquot portion was counted by a cell counter such as a haemocytometer to determine cell concentration of the sample. The proper cell concentration for immunization is obtained by dilution, by the addition of more salt solution to achieve a concentration of about 200 million epidermal cells per milliter. This first product is designated the epidermal cell suspension.

To determine cell viability, an aliquot of the cell suspension was diluted to a concentration of about 0.2 million cells per ml. An indicator dye is added, such as trypan blue available in the marketplace from Grand Island Biological Co., to a small amount of the diluted suspension and allowed to dwell briefly. This small sample is then counted on the haemocytometer. The dye does not permeate the cell walls of viable (alive) cells and thus they remain uncolored for counting. No attempt is made to segregate the viable from the dead cells of the suspension.

As is seen in Box 2 of FIG. 1, the next step is the introduction of the cell suspension as an antigen into the body of the female. Young adult females, here New Zealand strain rabbits were injected with the dissociated male rabbit epidermal cells several times a week, for from 4 to 8 weeks, the standard scheduling procedure to achieve hyperimmunization to build up antibody titers. The total amount of injected male cells is about 100 million (1. ml) per 1 kg. of body weight.

Turning now to the third step as shown in FIG. 1, female rabbits are used for the isolation of the crude antiserum. These are first immunized as per step 2 above, and then killed at the time of peak immunoglobulin G (IGG) buildup in the blood, which is usually 5 to 15 days after the final injection of immunizing male epidermal cells, depending upon the specie involved. It is understood of course that aseptic conditions are employed to minimize contamination of the antiserum. Exsanguination of the rabbits was the mode of killing employed with blood collection taking place in a series of suitable containers such as 50 ml syringes to which a minor amount of air is admitted to aid in the formation of a clot in each syringe. The blood collection syringes incubate at the body temperature of the specie, here 37° C. for rabbits for several hours until the clot forms and falls to the bottom of the container with supernatant liquid on top. This supernatant liquid which is the antiserum is centrifuged or otherwise treated to remove any residual blood cells. The various specimens of clarified supernatant antiserum are pooled together and complement -deactivated, ie. decomplemented, by heating in a circulating water bath or in another suitable apparatus. This is a standard immunological procedure. The decomplemented crude antiserum may then be either used immediately or stored by refrigeration prior to absorption against female rabbit spleen cells the next day, which spleen cells are prepared as will be described infra. The decomplementing step is not physically separate but only biologically incubates complement in the antiserum.

The packed female spleen cells are prepared as in step 4, by excising the spleens of dead female rabbits, dicing them into small pieces and dispersing them in a neutral salt solution in a blender at a relatively low speed to achieve single cell suspension. Strictly for convenience in handling I have found that 4 to 6 rabbit spleens may be mixed with HBSS in a weight to volume ratio of 1:5 to yield satisfactory results. The cell suspension is seived to remove debris and treated with a sedimentation promoting agent, the most common of which is a 5% solution of dextran sulfate to crosslink the red cells and cause aglutination whereby the red cells will settle out. The dextran sulfate is employed in a 1:9 or 1:10 ratio d.s./cell suspension according to the manufacturer's recommendation. The white blood cell (leukocyte)-rich supernatant is then centrifuged to obtain packed spleen leukocytes as a pellet. Optionally prior to this centrifugation step, a second sedimentation may be carried out to obtain larger yields, if desired. The centrifugation is allowed to proceed for a suitable time such as 10 minutes at 100 g, once or twice. The supernatant liquid over the packed cells should not be drawn off until the packed cell antiserum is ready for absorption per the next step. Preferably not more than about 4 hours is allowed to elapse prior to absorption in order to minimize cell death.

Step 5 is the serial absorption step to segrogate the monospecific male-specific antibody. Thus using standard absorption techniques, wherein 5 to about 10 volumes of undiluted crude antiserum prepared as in step 3 is added to each tube of packed female leukocytes, be they from spleen as above, or from bone marrow or epidermal cells that are female, the leukocytes are dispersed in the antiserum. The absorption is carried out by incubating the suspended cell/antiserum mixture at body temperature and then agitating the mixture at low temperature in a shaker bath. The cells are then centrifuged for a suitable time at adequate g force, example 10 minutes at 100 g. The partially absorbed anti-serum is transferred to a fresh tube or vessel of packed female leukocytes and the absorption process is repeated. The liquid is retained, while the leukocytes that absorb material from the liquid each time is discarded. Each time that the liquid was reused, it was noted, and on the 5th, 10th and 15th reuses, ie. absorptions, serially small aliquots were set aside for testing of the anti-male antigen specificity, as will be described below. It was found that the liquid remaining after the 15th serial absorption was monospecific for the male antigen as will be described below.

It is to be understood, that if necessary, the serial absorption procedure may be interrupted upon the completion of an individual absorption by storing the cell-/antiserum mixture under refrigeration at about 4° C.

Step 6 is the testing of the antiserum for male antigen specificity. In order to test for specificity, it is necessary to have control samples of leukocytes. Thus one prepares separate batches of male and female leukocytes, by either the process previously described in step 4, box 4 of FIG. 1, for female and a similar process with a substitution of male counterpart material in this process to prepare male leukocytes; or a separate process known to the art may be employed for such purpose, just so long as separate batches of 100% female and 100% male cells are established. The process described above or another process is carried out until packed cells are packed as by centrifugation (supra). The separate packed cells, here male bone marrow cells and separate female bone marrow cells are resuspended in a suitable solution, reduced in pH slightly toward the acid side, and spread out on microscope slides. A third sample comprised of 50% female and 50% male bone marrow cells is prepared by mixing exact amounts of the two separate samples together to achieve the 50:50 ratio. All three sets of microscope slides are then dyed by a fluorochrome and the samples were counted for percentage of cells that fluouresce from the fluorochrome. Typical among the resuspension agents known to the art for such purposes as set forth above is a solution of bovine serum albumin; phosphate buffered saline solution, ethylenediamine tetraacetic acid, (EDTA) and sodium bicarbonate at a pH of about 6.8. A class of fluorochrome that may be employed are the fluorscein isothiocyanate-conjugated mammal anti-mammallian specie being employed globulin. Here the conjugate was conjugated goat anti-rabbit globulin, available in the marketplace from Miles Laboratories, ELKHART Indiana. Material describing prior treatment of slides with male-specific antibody and washing antisera were judged specific for male antigen if specific fluorescence was found in essentially 100% of the male leukocytes; 50% of the cells obtained from the 50:50 mixture of male and female cells; and 0% of the cells from the female spleen leukocytes. Such results were obtained after fifteen runs.

Reference to step 7 of FIG. 1 indicates that the immunoglobulin fraction G is separated from the previously judged male specific antigen. The separation step involved to remove such undesired products as complement, albumen and lipoproteins can occur employing various accepted techniques. One such technique is known in the immunological field as salting out. In such a separation technique, all of the various fractions of immunoglobulin A through M are separated out as one large fraction. I prefer however to be more specific and thus I recommend the use of gel fractionation, another standard technique to isolate the largest fraction of desired immunoglobulin, the G fraction, which is in the molecular weight range of about 150,000.

As is known in the art, dextran sulfate and calcium chloride are stirred into small quantities, in the neighborhood of 50 to 100 ml of male-specific antiserum to precipitate and remove the lipoproteins, which are believed to be interfering substances for the intended use of the end product of this invention. The lipoproteins are removed by centrifugation.

Supernatant liquid from the just above centrifugation step is applied to a separation column containing a gel or bead capable of segregating the immunoglobulins into various molecular weight fractions. A typical material among many that may be used for such purpose is Bio-gel A-5 m, made by Bio-Rad Laboratories. A small amount of sodium chloride is added to create an isotonic solution. After collection of the various fractions, an optical density profile was prepared from spectrophotometric readings, as is known to the art. All of the immunoglobulin G (IgG) fractions were pooled for storage. It is believed that if the salting out technique were employed such that a total IG mixed fraction were obtained, the yield would be about 10 to 15% higher than the system just described yielded.

Pooled IgG fractions, or the large Ig A-M concentration is further concentrated by ultrafiltration, and adjusted to a final concentration after a spectrophotometric determination of protein concentration, to a useable 1mg IgG/ml level by the addition of PBS (phosphate buffered saline). Passage through a membrane to eliminate any possible concentration of IgG is stored until needed as by freezing at $-20$ degrees C.

By the procedure outlined above, yields of between 0.5 and 1.5 mg of anti-male antigen specific igG/ml of starting crude antiserum are obtained.

The total fraction of immunoglobulins A through M, as obtained by the salting out technique all contain the desired product, monospecific male-specific antibody. The process of gel fractionation often called gel filtration, gives rise to immunoglobulin G which contains the same monospecific male-specific antibody. However, the immunoglobulins are not pure male antibody. What has transpired is that all of the antibodies which are capable of reaction with female cells have been removed. This leaves a large spectrum of antibodies among which is the monospecific male-specific antibody. For example, non-removed antibodies in the immunoglobulin fractionation IgG, provided perhaps include antibodies against blood group antigens and antibodies reactive to pathogens experienced by the individual, all of which are proteinaceous materials.

Thus, the immunoglobulin fraction or the separate immunoglobulin G contains monospecific male-specific antibody free from male specificity interfering antibodies.

Thus, this explains why one carries out the serial absorption of the crude antiserum such that no specificity intering materials are present. However, the total process herein includes the use of the monospecific male-specific antibody found in the immunoglobulin for binding to an immunoabsorbent. In order to anticipate or prevent any non-specificity interfering proteins i.e., albumen, glyocproteins etc., present in the antiserum post serial absorption from interfering with the immunoabsorbent coupling reaction, I have included the step of segregating the immunoglobulin fraction or IgG from the antiserum to give a product containing the desired male-specific antibody that is now free from both specificity interfering antibodies, and coupling reaction interfering proteins. The following constitutes an illustrative non-limiting example.

SPECIFIC EXAMPLE

Preparation of Epidermal Cell Suspension

Young adult male New Zealand strain rabbits (3-5 kg body weight) were killed by exsanguination. Thoracic skin was shaved, washed with 70% ethanol, excised, scraped free of fat, and placed in Hank's balanced salt solution, (HBSS) pH 7.4. Square cm pieces of the skin were cut into 1-2 mm sized pieces and incubated for 1 hour at 37° C. in HBSS containing 0.1% trypsin. The incubations were agitated at low speed in a table top shaker bath. After incubation, epidermal cells were seived through fine, multiple layered nylon mesh and centrifuged at 100× g for 10 minutes. The supernatant was removed, and the cell pellet was resuspended in HBSS containing deoxyribonuclease (10 mg/l). The cells were then returned to the shaker bath for 20 minutes. This treatment dissociates remaining cellular aggregates and small clumps. The dissociated cells were twice washed (centrifuged as above and resuspended in HBSS) and pooled. An aliquot was counted by haemocytometer for cell concentration and viability. Cell preparations were judged at least 70% viable by this method. Cell concentration for immunization was adjusted by addition of HBSS to 100 million epidermal cells/ml.

Cell Viability Determination

An aliquot of cell suspension was diluted in HBSS to a concentration of 0.2 million cells/ml. 0.5 ml of diluted suspension and 0.1 ml of 0.4% trypan blue were placed in a 4 ml glass vial at room temperature for 5 minutes. The suspension was then counted in a haemocytometer. The percentage of viable cells were calculated on the assumption that cells excluding the dye were viable whereas stained cells were dead.

Immunization and Isolation of Crude Antiserum

Young adult female New Zealand strain rabbits (4–6 kg body weight) were each injected with 500 million (5.0 ml) dissociated male rabbit epidermal cells. The injections were delivered intraperitoneally twice weekly (3–4 days between successive injections) for 6 consecutive weeks. The female rabbits were exsanguinated 6 days after the final injection of immunizing male epidermal cells. The exsanguinations were performed by heart puncture using a needle attached to a 50 ml disposable syringe. The needle was removed from the syringe immediately after blood collection was completed. The plunger was drawn back slightly to admit a small amount of air into the barrel. The syringes were left upright in a rack in a 37° C. incubator for 2 hours. During this time, the clot formed and retracted to the bottom of the barrel. The supernatant serum was delivered into a series of 40 ml conical centrifuge tubes. Residual blood cells were removed from the antiserum by centrifugation at 800× g for 15 minutes. The clarified supernatant antiserum was withdrawn, pooled in a flask, and complement deactivated by heating in a circulating water bath at 56° C. for 30 minutes. The decomplemented crude antiserum was then refrigerated overnight prior to absorption against female rabbit spleen cells the next day.

Preparation of Packed Speen Cells

More young adult female New Zealand rabbits (3–6 kg body weight) were killed by neck fracture. The spleens were excised, rinsed in HBSS, diced into 1 cm pieces in HBSS, transferred to a Waring ® blender, and dispersed at low speed consistent with achieving a single cell suspension. Four to 6 individual rabbit spleens were used per batch at a HBSS to splenic tissue ratio (v/w) of approximately 5:1. The resultant cell suspension was seived through fine, multiple layered nylon mesh to remove the bulk of aggregated debris. A 5% solution of dextran sulfate (mol. wt. 250,000) was added to the seived cell suspension in a volume ratio of 1:9, respectively. Red blood cells were allowed to settle for 40 minutes. The white blood cell (leukocyte)-rich supernatant was then transferred to a series of 50 ml centrifuge tubes. The sedimented red blood cells were resuspended in an equal volume of HBSS containing 0.5% dextran sulfate and allowed to sediment a second time to increase the yield of leukocytes. The leukocytes were pooled, centrifuged at 100× g for 10 minutes, and washed twice as above in HBSS. The packed spleen leukocytes were obtained as a pellet by a final centrifugation at 100× g for 10 minutes, after which the tubes were refrigerated at 4° C. The supernatant over the packed cells was not drawn off until the antiserum was ready for absorption. Not more than 4 hours was allowed to elapse between the final packing of female spleen leukocytes and their use in absorption in order to avoid cell demise.

Serial Absorptions of the Crude Antiserum

Approximately ten volumes of undiluted decomplemented crude antiserum were added to the room temperature tubes for each volume of packed leukocytes. The leukocytes were dispersed in the antiserum by repeatedly drawing the cell pellet into a pipet. The absorption was carried out by first incubating the suspended cell/antiserum mixture 30 minutes at 37° C., followed by agitation for 2 hours at 4° C. in a table top shaker bath. The cells were centrifuged out at 100× g for 10 minutes. The partially absorbed antiserum was then transferred to a fresh tube containing packed female spleen leukocytes and the absorption repeated. This serial procedure was interrupted as needed by refrigerating the cell/antiserum mixture at 4° C. overnight. An aliquot of antiserum was taken after 5, 10 and 15 serial absorptions had been performed to test for anti-male antigen specificity. Testing for the male antigen after the 15th serial absorption indicated male specificity as desired. Such testing was carried in accordance with the procedure set forth infra.

Specificity Testing

Male and female rabbit marrow cells were prepared and kept separately as above up to the packed cell stage in HBSS. The packed cells of separate male and separate female samples each were then resuspended in an equal volume of a solution containing 20 ml 20% bovine serum albumin, 60 ml of 0.1 M phosphate-buffered saline (PBS), 8 ml 5% ethylenediamine-tetraacetic acid, and sodium bicarbonate added to pH 6.8. A third suspension was prepared by mixing equal volumes of the suspended male and female marrow cells. Drops of each suspension were spread onto separate glass microscope slides, air dried, coded, and stored in closed boxes at −20° C. until used in testing. For testing, slides were placed 30 minutes in a bath of phosphate-buffered saline, pH 7.4 (PBS), stirred by magnetic bar. The slides were next placed on a horizontal surface and flooded for 30 minutes with a 1:10 PBS dilution of the antiserum. The slides were placed in a stirred PBS bath for another 30 minutes, then replaced on the horizontal surface and flooded with a 1:10 PBS dilution of fluorescein isothiocyanate-conjugated goat anti-rabbit globulin, available from Miles Laboratories. The slides were finally washed for 1 hour in a stirred PBS bath, mounted in glycerol containing 10% PBS by volume, and counted for percentage fluorescent cells under a fluorescent microscope. Antisera samples were judged specific for male antigen by this test after the 15th serial absorption test.

Antiserum Fractionation

Absorbed antisera previously judged male antigen-specific were fractionated by a gel filtration system which isolated the immunoglobulin class G (IgG) fraction of serum proteins. This procedure employed fifty ml amounts of male-specific antiserum which were first gently stirred with a mixture of 1.0 ml dextran sulfate (mol. wt. 500,000) and 5.0 ml 1 M calcium chloride for 15 minutes at room temperature. The precipitated lipoproteins were centrifuged out at 6000× g for 10 minutes. Ten ml amounts of the supernatant were applied to the top of a 4×60 cm column containing Bio-gel A-5 m, and equilibrated with 0.1 M Tri-HCl buffer, pH 8.0, containing 0.2 M sodium chloride. Fractions were eluted with the same buffer at 6 ml/hour Three ml fractions were collected and an optical density profile was prepared by spectrometer readings at 280 millicrons. The fractions from the large peak comprising IgG were pooled together. They were set aside for use in coupling to the immunoabsorbent agent.

USE OF MONOSPECIFIC MALE-SPECIFIC ANTIBODY

As will be explained in more detail below, the immunoglobobulin total fraction or the immunoglobulin G segment thereof contain tain the desired product monospecific male-specific antibody in such fractions. By the process previously recited, the fraction(s) have been deprived of other proteinaceous material that could or would tend to interfere with the male specificity which is needed for the separation of male determineing from female determining spermatozoa. For this invention, male antibody need not be isolated.

As will be understood by those having ordinary skill in the art of immunology, the just described technique of raising and refining the required male-specific antiserum or anti-Y antiserum is adapted to assure the monospecificity of the antiserum. That is, to assure that the antiserum thereby raised and refined, and intended for application in sperm fractionation, will contain antibody capable of binding to the Y antigen, but to no other antigens, expressed by sperm surface membranes. Anti-sperm antibodies other than anti-Y or male-specific could diminish both the precision of the sperm fractionation process of my invention and the fertility of the resulting seminal fluid material of my invention.

If the male-specific antibody is frozen prior to its usage for coupling to an immunoabsorbent in accordance with another portion of my invention, there could be some loss of specificity if more than one freeze-thaw cycle has occurred during storage. To verify specificity, one may conduct the specificity test previously discussed or another similar test to be set forth currently. The monospecificity of the male-specific antiserum may be tested by coupling a portion of it with fluorescein isothyiocyanate. In carrying out this test, the fluorescent-tagged antiserum is combined with human spermatozoa in a direct fluorescense microscopic preparation. Bright fluorescence of approximately 50 percent of the sperm indicate specific binding of the fluorescent tagged male-specific antiserum by Y sperm. The lack of staining of the remaining approximately 50 percent of the sperm, i.e. the X sperm, indicates the essential monospecificity of the anti-serum produced byd antiserum monospecificity test, if it were shown in FIG. 2, would immediately follow the agarose gel chromatography indicated in the step of reference numeral 18.

After the above-described monospecificity test, the refined antiserum is coupled to a solid-phase immunoabsorbent material, as noted under reference numeral 18.

It is noted that, in accordance with a particular aspect, it is preferred to alter the concentration of the bulk portion of the antiserum to one milligram per milliliter in phosphate buffered saline, pH 7.4, prior to immunoabsorbent coupling.

The said immunoabsorbent coupling, i.e., coupling of the previously produced male-specific antibodies to solid-phase immunoabsorbent material may be carried out as follows.

EXAMPLE 2

Sephadex G-200 beads (Pharmacia) are seived to provide 60 milliliters of beads to a size of 80 to 120 microns. The thus-seived beads are "activated" with 100 milligrams of cyanogen bromide at pH 10.2 for 10 minutes, resulting in a 20 to 30 percent reduction in volume. This activation treatment renders the immunoabsorbent material capable of accepting protein molecules by covalent binding. The activated beads are washed in borate-burrered saline at pH 8.3. 20 milligrams (20 milliliters) of monospecific male-specific antibody are added to the washed, activated beads, which first have rested at room temperature for about 4 hours without mechanical stirring. The resulting Sephadex G-200, loaded with male antibody is called a conjugate. Anti-Y antibody conjugate is washed with phosphate-buffered saline without suction, mixing every 15 minutes with a glass rod.

The thus washed anti-Y conjugate is used to prepare a series of columns by packing 12 milliliter plastic, disposable syringes, fitted with a polyethylene retainer disk at the bottom instead of a piston, with eight to ten milliliters of the conjugate. While any column could have been employed, this was a convenient one to use.

These columns are washed prior to sperm fractionation with medium 199 with added 50 percent fetal calf serum by volume, 2.5 millimolar ethylenediamine tetraacetic acid by weight and 1 percent penicillin streptomycin by volume (hereinafter called "Medium no. 1").

Having thus prepared the fractionation columns (reference numeral 20 in the drawing), live sperm (reference numeral 22 in the drawing) may now be prepared for fractionation in accordance with the method of my invention by the following technique.

The live sperm are dispered in Medium no. 1 and then centrifuged gently. The non-cellular supernatant is decanted from the centrifugation vessel, and then the sedimented sperm are resuspended in fresh Medium no. 1. The sperm suspension in fresh Medium no. 1 is centrifuged gently, and the supernatant non-cellular material again decanted from the centrifugation vessel. The sedimented sperm from the second decanting step is then resuspended in a new medium which is designated Medium no. 2. This is a mixture of a commercial medium designated 199 to which is added 50 percent fetal calf serum by volume and 2.5 millimolar ethylenediamine tetraacetic acid by weight. This new medium no. 2 has a pH of 7.4 The sedimented sperm in Medium no. 2 has a concentration of 10 to 20 million cells per milliliter. This sperm suspension, sometimes hereinafter called the "prepared sperm suspension", is ready for application to the prepared immunoabsorbent columns.

As indicated in the drawing by reference numeral 24, the prepared sperm suspension may now be applied to the previously prepared fractionation columns in accordance with the following technique

LOADING TO SEPARATE

A 5 to 10 milliliter portion of the just described prepared sperm suspension is applied by syringe to several 8 milliliter columns at room temperature. Eluates comprising the X sperm fraction are collected from the columns by stepwise elution with 15 milliliter amounts of the abovesaid Medium no. 2 at flow rate of approximately 0.3 to 0.5 milliliters per minute, continued until the effluent is virtually cell-free. This elution of the female-determining sperm is indicated by the reference numeral 26 in the 2nd figure. Any eluate liquid can be used provided that it is not detrimental to male determining sperm, to separate the female sperm which is located in the spaces between the beads.

Having eluted substantially all of the female-determining spermatozoa from the fractionation columns, the male-determining spermatozoa may be recovered from the fractionation columns in accordance with the following technique.

A quantity of said Medium no. 2 is supplemented with 10 milligrams of male-specific antibody per milliliter. This antibody-supplemented medium hereinafter is called "Medium no. 3".

Eluates comprising the male-determining spermatozoa are collected from the fractionation columns by stepwise elution with 15 milliliter amounts of Medium no. 3.

As seen in the drawing, such elution with Medium no. 3 subserves the two steps of adding free antibody to the fractionation columns (reference numeral 28) and eluting the male-determining spermatozoa from the fractionation columns (reference numeral 30).

As will be evident to those having ordinary skill in the art of immunology, the male-determining sperm fraction is eluted from the fractionation columns, in accordance with the principles of the present invention, by employing the well-known principle of competitive inhibition of cellular binding.

In accordance with a further teaching of the present invention, the contents of the fractionation columns will preferably be gently mixed during the elution of the male-determining sperm fraction by carefully drawing the immunoabsorbent beads up and down in a Pasteur pipet. Further, in accordance with the teachings of the present invention, this gentle mixing action by pipet will preferably be continued until the effluent from the fractionation columns is virtually cell-free as determined microscopically.

In accordance with another aspect of the present invention, it is preferred that the male-determining and female-determining sperm eluates both be washed, i.e., centrifuged and then resuspended, three times in medium 199 containing 5% fetal calf serum by volume, said mixture being called "Medium no. 4", prior to testing for remaining fractional content of undesired sperm. This procedure places the sperm into a holding medium for storage prior to insemination artificially.

While the just described technique of freeing immunoabsorbent-bound male-determining sperm from the fractionation columns, employing the principle of competitive inhibition, may be successfully used in carrying out the method of my invention, it is to be understood that the method of my invention is not limited to the employment of this particular competitive inhibition technique, since alternative techniques are well-known to those having ordinary skill in the art of immunology. Such alternative techniques include enzymatic digestion of the immunoabsorbent and alteration of pH or salt concentration of the medium. Other techniques will occur to those having ordinary skill in the art of immunology without the exercise of invention.

Seminal fluids for artificial insemination material of my invention, prepared by the steps and techniques set out hereinabove, have been tested for (i) the efficacy of separation in sperm suspensions prepared from one species of mammal and (ii) the fertility of the separated sperm fractions in a second species of mammal.

Efficacy according to (i) was measured by criteria of total cell recovery and degree of X and Y sperm separation attained in the fractions. The quinacrine fluorochrome, a cellular stain known in the prior art to be specific for the presence of the Y chromosome in human sperm, was used in this test. The results of this test showed that Y fractions containing 89 percent or more of Y positive cells and X fractions containing 6 percent or fewer of Y positive cells were obtained with a sperm loss of 18 percent or less (Table I).

Fertility according to (ii) was measured by sex preselection trials in mice. Pooled epididymal and vas deferens sperm from male mice were fractionated and brought to a concentration of five million sperm per 0.1 milliliter in Medium no. 4. Recipient females were each inseminated with five million sperm at 24 to 30 hours post partum. Control females were mated to male mice at 24 to 30 hours post partum. The results showed that insemination with male-determining seminal fluids or female-determining seminal fluids prepared in accordance with the method of my invention strongly preselected the sex of the offspring, resulting in fewer than ten percent of undesired issue by sex (Table II).

These data are statistically significant at the level of 0.001 by Chi Square test. The fact that a 60 percent conception rate was achieved in this test speaks well for the fertility of the seminal fluids or artificial insemination materials produced by the method of my invention, when compared with the well-known technical difficulties in the artificial insemination of mice as shown by the comparable conception rates which were obtained in trials with unfractionated mouse sperm suspension. The offspring sex ratios attained in these tests (Table II) conform closely to the sex ratios expected on the basis of residual contamination of the inseminated fractions by sperm of the undesired sex chromosome type as observed in the fluorescent male-specific antibody staining tests referred to hereinabove. It is believed, then, that the expected sex ratio to be achieved by any particular batch of seminal fluid or artificial insemination material of the present invention can therefore be predicted by such testing.

It is believed to be apparent from the foregoing that an anti-male-rabbit-specific antibody raised in female rabbits treated in accordance with a method of my invention to produce artificial insemination materials of my invention, can effect a separation of male-determining and female-determining spermatozoa in semen from mice and humans. This result accords with data from the scientific literature which indicate that the Y antigen of mammals exhibits the property of extensive immunological cross-reactivity between species.

It is particularly noted that the method of the present invention, employing as it does a solid-phase immunoabsorbent system which permits mammalian X and Y sperm to be separated by differential binding of Y sperm to the immunoabsorbent, rather than by mechanical methods relying upon the very small differential density between X sperm and Y sperm, is fully reversible so that Y sperm or male-determining sperm can be recovered without the cellular damage attending conventional cellular agglutination, cytolysis or other means of cellular inactivation. It is believed that the importance of these properties of the method of my invention for fertility and precision in separated sperm fractions intended for sex preselective artificial insemination purposes cannot be overestimated.

When one binds the Y sperm to the surface of the bead, this can be readily removed by adding excess free antibody in solution to column. This illustrates competitive inhibition of binding.

The test data from the efficacy test (i) and fertility test (ii) referred to above are as follows:

TABLE I

Human X and Y sperms before and after fractionation using immunoabsorbent-anti-Y antibody conjugate.

| Trial # | Y positive cells (%)[1] | | | Sperm Recovery (%)[2] |
| --- | --- | --- | --- | --- |
| | Unfractionated | X fraction | Y fraction | Total Recovery of Sperm |
| 1 | 47 | 2 | 92 | 82 |
| 2 | 48 | 5 | 93 | 82 |
| 3 | 45 | 4 | 90 | 88 |
| 4 | 48 | 6 | 89 | 89 |

[1]Based on counts of 200 quinacrine stained cells/category
[2]Based on dividing cells in combined fractions by cell input into columns.

TABLE II

Sex preselective capacity of mouse sperm fractionated by means of anti-Y coated immunoabsorbent.

| | Male Births (%)[1] | |
| --- | --- | --- |
| Control | X Fraction | Y Fraction |
| 46.6 | 4.2 | 92.3 |

[1]Based on 150 or more births/category.

From the foregoing, it is believed to be apparent that the completely immunological and not-mechanical, method of my invention has great utility in controlling the sex of mammalian offspring. It is further believed that the method, apparatus, and artificial insemination material of my invention are especially important in commercial application in the field of animal husbandry for example, in permitting the breeder or farmer to have a choice in selecting the sex of animal offspring. By way of illustration, the dairy farmer can elect to obtain only female offspring and thereby breed only milk-producing cows, rather than bulls. Regarding human procreation, my invention provides patents with a simple, easily employed means to select or control the sex of the offspring, in that they may satisfy the desire to have a child of a particular sex, thus limiting family size and contributing to the reduction of world population problems.

It is to be seen that in the preparation of the male-specific monospecific antibody that various materials can be substituted for these employed in the several steps of this process. Thus, male cells may be obtained from male mammalian epidermis, spleen, bone marrow, thymus, lymph nodes and perhaps other tissues as well, within the skill of an immunologist.

Female cells for the absorption step may be obtained from any of the above type of cells from a female mammal.

It is to be understood that the absorption step must be carried out against female cells of the same specie from which the original male cells were obtained. In addition, the same requirement of similar specie is maintained for the female mammal which received the antigen. Thus if rabbit male cells were obtained, the antigen must be placed into a female rabbit and the absorptions carried out against female rabbit cells. The limitation of similar mammal for this requirement is as to specie only, and not as to strain.

The male antibody product may be employed with any mammal and need not be limited to use with the same mammal specie from which the original male cells that produced the monospecific male-specific antibody were obtained. It is believed, therefore, that cells obtained from a male rat could be used for breeding of male cattle if desired. While no testing has been carried out, it is further believed that since the male-specific antibody is not specie specific, that male antibody produced from rabbits could be used for male sperm preparation for female human sperm separation by the immunoabsorbent technique disclosed herein.

In the specificity test procedure, most types of suitable cells may be employed, be they marrow, thymus, etc., that will give correct test results. While it is believed that the cells used here may be from any specie of mammal, the operator may prefer to use cells of the same specie in which the antigen was implanted for antiserum preparation.

In the method of preparation of the antibody, variations in each step of the procedure are possible within the skill of the art. Thus, the serial absorption step need not be carried out as described in detail against prekilled females to obtain packed spleen cells as described above. If desired, a spleenectomy easily accomplished by one skilled in the art, can be used to obtain a donor spleen as the source of the packed spleen cells Furthermore, it is possible and it is within the scope of the invention to serially absorb against a series of living female animals of the same specie, in vivo, followed by permitting the antigen to react with the female cells in vivo for a suitable period of time, further followed by a killing off of the particular female to obtain serum therefrom for use in the next serial absorption.

It is seen therefore, that the process step merely pertains to the concept of serially absorbing against female cells, per se rather than to a specific mode of absorbing.

For that matter, to further illustrate the breadth of the invention, referring back to a combination of steps 1 and 2, a solid graft of male tissue may be implanted into or onto a female recipient of the same specie in lieu of injection of dissociated male cells to obtain crude antiserum. Here the implant will cause an immunoglobulin synthesis to occur, which is permitted per the next step to buildup.

In the discussion above, it is seen that the technology has related to the preparation of an antibody, namely the monospecific male-specific antibody which is then coupled to an immunoabsorbent and this combination is used to fractionate spermatozoa as discussed herein. It should also be appreciated that in the second portion of this invention, another antibody having a different specificity, namely an anti-immunoglobulin having specificity for the mono-specific male-specific antibody, may be coupled to the immunoabsorbent. Such a coupled anti-immunoglobulin immunoabsorbent will "recognize" and bind to male determining sperm which have been pre-bound to the monospecific male-specific antibody.

Thus, the column per box 20 of FIG. 2 would consist of anti-immunoglobulin coupled immunoabsorbent to which live sperm per box 22 would be added, but only after the live sperm had been pretreated with monospecific male-specific antibody. The male determining sperm will then be preferentially bound to the column and the unbound female determining sperm will be eulted per box 26 of FIG. 2. The balance of the process, namely steps 28 and 30 would be the same. Step 28 may be carried out using monospecific male-specific antibody to be added to the column to remove the bound male determining sperm by competitive inhibition of binding. Alternatively, it would also be possible to remove the male determining sperm by the addition of more anti-immunoglobulin antibody to the column. To practice this alternative embodiment, one may procure anti-immunoglobulin in the marketplace from any of many vendors for example, Flow Laboratories, McLean, Virginia.

As is well known in the art, the particular anti-immunoglobulin would depend on the species in which the mono-specific male-specific antibody was raised. That is, when the male-specific antibodies are raised in rabbits, as in the preferred embodiment herein, the anti-immunoglobulin will be anti-rabbit antibody raised in another mammalian species, such as sheep, mice, rats and the like. Thus, the immunoabsorbent zone prepared with the anti-rabbit antibody would preferentially bind the conjugates comprising the male-determining sperm and mono-specific male-specific antibody, but would not bind the female-determining sperm which have cell surface antigens not found on rabbit cells.

Since certain changes may be made in the above compositions and processes without departing from the scope of the invention herein involved, it is intended that all matter contained in the above description and shown in the accompanying drawings shall be interpreted as illustrative only and not in a limiting sense.

I claim:

1. A process for separating male and female determining sperm from native semen which comprises:
    (a) treating the native semen with excess monospecific male-specific antibody free from male-specificity interfering antibodies and coupling reaction interfering proteins to form comjugates between the male determining sperm and the antibodies,
    (b) coupling anti-immunoglobulin antibody capable of specifically binding said male-specific antibody to a solid phase immunoabsorbent substrate, said substrate having a form capable of being loaded into a separation column,
    (c) loading a separation column with the conjugate of the solid phase immunoabsorbent and anti-immunoglobulin antibody,
    (d) passing the treated semen containing male and female determining sperm through the column, whereby the male determining sperm and male-specific antibody conjugates are bound to the solid phase immunoabsorbent, while the female determining sperm passes out of the column, and
    (e) separating out the male determining sperm from the column.

2. The process of claim 1 wherein the step of separating out the male determining sperm comprises passing a composition consisting essentially of monospecific male specific antibody through the column.

3. The process of claim 1 wherein the step of separating the male determining sperm comprises passing a composition consisting essentially of anti-globulin antibody through the column.

4. The process of claim 1 wherein the coupling step (b) comprises:
    activating the solid phase immunoabsorbent material to render it capable of accepting a protein by covalent bonding, an
    adding a solution of anti-globulin specific antibody thereto.

5. As a new composition of matter, an antibody composition containing monospecific male-specific antibody free from specificity interfering antibodies and coupling reaction interfering proteins.

6. As a new composition, a conjugate of activated solid phase immunoabsorbent material having anti-globulin specific antibody capable of binding male-specific sperm distributed over the surface of said immunoabsorbent material, and coupled thereto 7. The method of increasing the percentage of mammalian offspring of either sex, comprising the step of selectively separating male-determining spermatozoa by treating a body of semen with male-specific antibody, and contacting the treated semen with anti-globulin antibody capable of binding male-specific sperm, said anti-globulin antibody being coupled to immunoabsorbent material.

* * * * *